(12) United States Patent
Schaff et al.

(10) Patent No.: US 9,304,129 B2
(45) Date of Patent: Apr. 5, 2016

(54) DEVICES, SYSTEMS, AND METHODS FOR CONDUCTING ASSAYS WITH IMPROVED SENSITIVITY USING SEDIMENTATION

(71) Applicant: Sandia Corporation, Albuquerque, NM (US)

(72) Inventors: Ulrich Y. Schaff, Livermore, CA (US); Chung-Yan Koh, Dublin, CA (US); Gregory J. Sommer, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/597,601

(22) Filed: Jan. 15, 2015

(65) Prior Publication Data

US 2015/0125346 A1    May 7, 2015

Related U.S. Application Data

(60) Division of application No. 13/423,050, filed on Mar. 16, 2012, now Pat. No. 8,962,346, which is a continuation-in-part of application No. 12/891,977, filed on Sep. 28, 2010, now Pat. No. 8,945,914.

(60) Provisional application No. 61/362,398, filed on Jul. 8, 2010, provisional application No. 61/362,407, filed on Jul. 8, 2010.

(51) Int. Cl.
*B01L 3/00* (2006.01)
*G01N 33/543* (2006.01)
(Continued)

(52) U.S. Cl.
CPC ...... *G01N 33/54313* (2013.01); *B01L 3/50215* (2013.01); *B01L 3/502753* (2013.01);
(Continued)

(58) Field of Classification Search
None
See application file for complete search history.

(56) References Cited

U.S. PATENT DOCUMENTS

| 3,555,284 A | 1/1971 | Anderson |
| 3,744,974 A | 7/1973 | Maddox |

(Continued)

FOREIGN PATENT DOCUMENTS

| WO | WO-2008/143578 | 11/2008 |
| WO | WO-2009/098237 | 8/2009 |

OTHER PUBLICATIONS

Abi-Samra, Kameel et al., "Infrared controlled waxes for liquid handling and storage on a CD-microfluidic platform", The Royal Society of Chemistry; Lab on a Chip, 2011, 723-726.
(Continued)

*Primary Examiner* — Melanie Y Brown
*Assistant Examiner* — Rebecca Martinez
(74) *Attorney, Agent, or Firm* — Dorsey & Whitney, LLP

(57) ABSTRACT

Embodiments of the present invention are directed toward devices, systems, and method for conducting assays using sedimentation. In one example, a method includes layering a mixture on a density medium, subjecting sedimentation particles in the mixture to sedimentation forces to cause the sedimentation particles to move to a detection area through a density medium, and detecting a target analyte in a detection region of the sedimentation channel. In some examples, the sedimentation particles and labeling agent may have like charges to reduce non-specific binding of labeling agent and sedimentation particles. In some examples, the density medium is provided with a separation layer for stabilizing the assay during storage and operation. In some examples, the sedimentation channel may be provided with a generally flat sedimentation chamber for dispersing the particle pellet over a larger surface area.

17 Claims, 10 Drawing Sheets

(51) Int. Cl.
  *G01N 33/558* (2006.01)
  *G01N 21/64* (2006.01)
  *G01N 15/04* (2006.01)
  *B82Y 15/00* (2011.01)
(52) U.S. Cl.
  CPC .......... *G01N21/6428* (2013.01); *G01N 33/558* (2013.01); *B01L 2200/0668* (2013.01); *B01L 2200/0673* (2013.01); *B01L 2400/0409* (2013.01); *B82Y 15/00* (2013.01); *G01N 15/04* (2013.01)

(56) References Cited

U.S. PATENT DOCUMENTS

| | | | |
|---|---|---|---|
| 4,125,375 | A | 11/1978 | Hunter |
| 4,156,570 | A | 5/1979 | Wardlaw |
| 4,656,143 | A | 4/1987 | Baker et al. |
| 4,683,579 | A | 7/1987 | Wardlaw |
| 4,844,818 | A | 7/1989 | Smith |
| 5,279,936 | A | 1/1994 | Vorpahl |
| 5,635,362 | A | 6/1997 | Levine et al. |
| 5,705,628 | A | 1/1998 | Hawkins |
| 5,882,903 | A | 3/1999 | Andrevski et al. |
| 6,153,148 | A | 11/2000 | Thomas |
| 6,319,469 | B1 | 11/2001 | Mian et al. |
| 6,503,722 | B1 | 1/2003 | Valkirs |
| 6,887,384 | B1 | 5/2005 | Frechet et al. |
| 7,033,747 | B2 | 4/2006 | Gordon et al. |
| 7,157,049 | B2 | 1/2007 | Valencia et al. |
| 7,758,810 | B2 | 7/2010 | Lee et al. |
| 2001/0055812 | A1 | 12/2001 | Mian et al. |
| 2002/0098535 | A1 | 7/2002 | Wang et al. |
| 2002/0137068 | A1 | 9/2002 | Haugland et al. |
| 2002/0151043 | A1 | 10/2002 | Gordon |
| 2002/0164659 | A1 | 11/2002 | Rao et al. |
| 2003/0124719 | A1 | 7/2003 | Woodside |
| 2004/0072278 | A1 | 4/2004 | Chou et al. |
| 2005/0215410 | A1 | 9/2005 | Merino et al. |
| 2005/0282220 | A1* | 12/2005 | Prober et al. ............ 435/6 |
| 2009/0004059 | A1 | 1/2009 | Pugia et al. |
| 2009/0069554 | A1 | 3/2009 | Finne |
| 2009/0209402 | A1 | 8/2009 | Andersson |
| 2009/0325186 | A1 | 12/2009 | Hinnah et al. |
| 2010/0068754 | A1 | 3/2010 | Kirakossian |
| 2010/0120596 | A1 | 5/2010 | Froman et al. |
| 2010/0151560 | A1 | 6/2010 | Wo et al. |

OTHER PUBLICATIONS

Ahanotu, et al., "Staphylococcal Enterotoxin B as a Biological Weapon: Recognition, Management, and Surveillance of Staphylococcal Enterotoxin", Applied Biosafety; vol. 11 (3), 2006, 120-126.
Albrecht, J.W. et al., "Micro Free-Flow IEF Enhanced Active Cooling and Functionalized Gels", Electrophoresis, 2006, pp. 4960-4969, vol. 27.
Amersham, "Percoll: Methodology and Applications", 2001, 1-84.
Amukele, et al., "Ricin A-chain activity on stem-loop and unstructured DNA substrates.", Biochemistry; vol. 44(11), Mar. 25, 2005, 4416-4425.
Andersson, et al., "Parallel nanoliter microfluidic analysis system", Clinical Chemistry, 2007.
Baldwin, Robert L. , "How Hofmeister Ion Interactions Affect Protein Stability", Biophysical Journal; vol. 71, Oct. 1996, 2056-2063.
Berry, Scott M., "One-step Purification of Nucleic Acid for Gene Expression Analysis via Immiscible Filtration Assisted by Surface Tension", Lap Chip, May 21, 2011.
Boyko, Matthew et al., "Cell-Free DNA—a Marker to Predict Ischemic Brain Damage in a Rat Stroke Experimental Model", Journal of Neurosurg Anesthesiol, vol. 23, No. 3, Jul. 2011, 222-228.
Brigotti, et al., "Shiga toxin 1 acting on DNA in vitro is a heat-stable enzyme not requiring proteolytic activation", Biochimie Journal; 86(45), 2004, 305-309.
Carney, J. , "Rapid Diagnostic Tests Employing Latex Particles", Analytical Proceedings, Apr. 1990, 99-100.
Curtis, R. A. et al., "A Molecular approach to bioseparations: Protein-protein and protein-salt interactions", Chemical Engineering Science; vol. 61, 2006, 907-923.
Czeiger, David et al., "Measurement of Circulating Cell-Free DNA Levels by a New Simple Fluorescent Test in Patients With Primary Colorectal Cancer", Am J Clin Pathol, 2011, 264-270.
Endo, et al., "RNA N-Glycosidase Activity of Ricin A-chain. Mechanism of Action of the Toxic Lectin Ricin on Eukaryotic Ribosomes", The Journal of Biological Chemistry, vol. 262, No. 17, Jun. 15, 1987, 8128-8130.
Glorikian, Harry et al., "Smart-consumables product development: Implications for molecular diagnostics", DX Direction, 2010, 12-16.
Glorikian, H. et al., "Overview of Microfluidic Applications in IVDS", DX Direction 1, pp. 12-16 (2010).
Goldshtein, Hagit et al., "A Rapid Direct Fluorescent Assay for Cell-Free Dna Quantification in Biological Fluids", Annals of Clinical Biochemistry, 2009, 488-494.
Gorkin et al., "Centrifugal microfluidics for biomedical applications", www.rsc.org/loc; Lab on a Chip, May 2010, 1758-1773.
Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.
Holmes, David et al., "Leukocyte analysis and differentiation using high speed microfluidic single cell impedance cytometry", Lab on a Chip 9, Aug. 7, 2009, 2881-2889.
Huang, et al., "The Primary Structure of Staphylococcal Enterotoxin B. III. The Cyanogen Bromide Peptides of Reduced and Aminoethylated Enterotoxin B, and the Complete Amino Acid Sequence.", The Journal of Biological Chemistry vol. 245 No. 14, Jul. 25, 1970, 3518-3525.
International Search Report and Written Opinion dated Jun. 28, 2013 for PCT/US2013/032349.
Lee, et al., "Fully integrated lab-on-a-disc for simultaneous analysis of biochemistry and immunoassay from whole blood", Lab Chip, 2011.
Lee, B. S. et al., "A fully automated immunoassay from whole blood on a disc", Lab on a Chip 9, Mar. 5, 2009, 1548-1555.
Lim, C. T. et al., "Bead-based microfluidic immunoassays: The next generation", Biosensors Bioelectronics 22, Jul. 20, 2006, 1197-1204.
Lo, C.T. et al., "Photopolymerized Diffusion-Defined Polyacrylamide Gradient Gels for On-Chip Protein Sizing", The Royal Society of Chemistry, Lab on a Chip, vol. 8, No. 8, 2008, pp. 1273-1279.
Lo, Y. M. D. et al., "Plasma Dna as a Prognostic Marker in Trauma Patients", Clinical Chemisty 46:3, 2000, 319-323.
Madou, Marc et al., "LAB on a CD", Annual Rev. Biomed Eng 8, May 2006, 601-628.
Maes, Melissa L. et al., "Comparison of Sample Fixation and the use of LDS-751 or anti-CD45 or Leukocyte Identification in Mouse Whole Blood for Flow Cytometry", Journal of Immunological Methods, 319(1-2) Jan. 30, 2007, 79-86.
Min, Junhong et al., "Functional Integration of Dna Purification and Concentration Into a Real Time Micro-PCR Chip", The Royal Society of Chemistry; Lab on a Chip, 2011, 259-265.
Price, Christopher P. et al., "Light-Scattering Immunoassay", Principles and Practice of Immunoassay (Second Edition); Chapter 18, 1997, 445-480.
Rhodes, Andrew et al., "Plasma DNA concentration as a predictor of mortality and sepsis in critically ill patients", Critical Care, 2006, 1-7.
Rider, Todd H. et al., "A B Cell-Based Sensor for Rapid Identification of Pathogens", www.sciencemag.org; Science vol. 301, Jul. 11, 2003, 213-215.
Riegger, L. et al., "Read-out concepts for multiplexed bead-based fluorescence immunoassays on centrifugal microfluidic platforms", Sensors and Actuators A—Physical, 2006, 455-462.
Saukkonen, et al., "Cell-Free Plasma DNA as a Predictor of Outcome in Severe Sepsis and Septic Shock", Clinical Chemistry; vol. 54:6, 2008, 1000-1007.

(56) References Cited

OTHER PUBLICATIONS

Schaff, et al., "Whole Blood Immunoassay Based on Centrifugal Bead Sedimentation", Clinical Chemistry Automation and Analytical Techniques 57:5, 2011, 753-761.

Schembri, et al., "Portable Simultaneous Multiple Analyte Whole-Blood Analyzer for Point-of-Care Testing", Clinical Chemistry 38/9, 1992, 1665-1670.

Schneider, et al., "Characterization of EBV-Genome Negative "Null" and "T" Cell Lines Derived From Children With Acute Lymphoblastic Leukemia and Leukemic Transformed Non-Hodgkin Lymphoma", International Journal of Cancer; 19(5), May 15, 1977, 621-626.

Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.

Zhang, L. et al., "A New Biodosimetric Method: Branched Dna-Based Quantitative Detection of B1 Dna in Mouse Plasma", The British Journal of Radiology, vol. 83, Aug. 2010, 694-701.

Ziegler, Annemarie et al., "Circulating DNA: a new diagnostic gold mine?", Cancer Treatment Reviews, vol. 28, 2002, 255-271.

McBain et al., Polyethyleneimine functionalized iron oxide nanoparticles as agents for DNA delivery and transfection, Journal of Materials Chemistry, 17, pp. 2561-2565, available online Apr. 13, 2007.

Riahi et al. Analytical Chemistry. 2011. 83(16): 6349-6354 and Supporting Information.

Melting Temperature Calculation. Retrieved on asf from the internet: http://www.biophp.org/minitools/melting_temperature/demo. php?primer=CGT+TAC+CCG+CAG&basic-1 &NearestNeighbor=1&cp=200&cs=50&cmg=0.

Berlier et al. The Journal of Histochemistry and Cytochemistry. 2003. 51(12): 1699-1712.

* cited by examiner

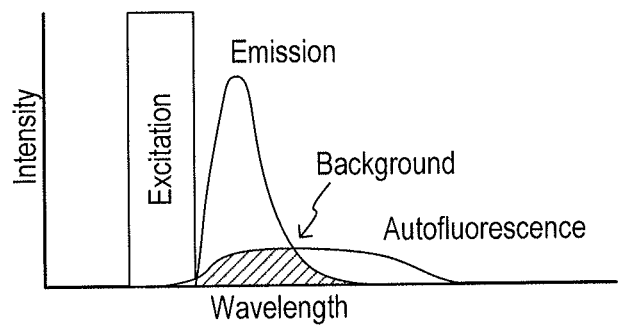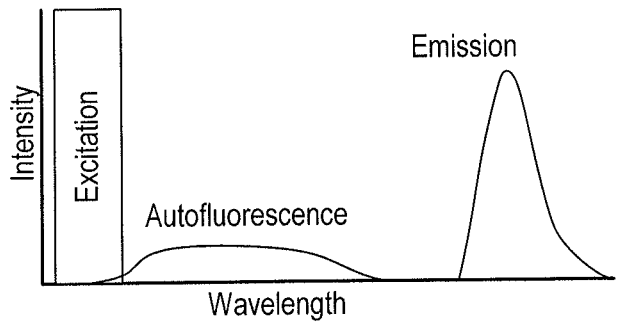
Figure 6

DEVICES, SYSTEMS, AND METHODS FOR CONDUCTING ASSAYS WITH IMPROVED SENSITIVITY USING SEDIMENTATION

CROSS-REFERENCE TO RELATED APPLICATION(S)

This application is a divisional of co-pending U.S. application Ser. No. 13/423,050, filed Mar. 16, 2012, entitled "DEVICES, SYSTEMS, AND METHODS FOR CONDUCTING ASSAYS WITH IMPROVED SENSITIVITY USING SEDIMENTATION", which is a continuation-in-part of U.S. application Ser. No. 12/891,977, filed Sep. 28, 2010, entitled "DEVICES, SYSTEMS, AND METHODS FOR CONDUCTING SANDWICH ASSAYS USING SEDIMENTATION", which application claims the benefit of Provisional Application No. 61/362,398, filed Jul. 8, 2010, and Provisional Application No. 61/362,407, filed Jul. 8, 2010. These applications are incorporated herein by reference in their entirety, for any purpose.

STATEMENT REGARDING RESEARCH & DEVELOPMENT

This invention was developed under Contract DE-AC04-94AL85000 between Sandia Corporation and the U.S. Department of Energy. The U.S. Government has certain rights in this invention.

TECHNICAL FIELD

Embodiments of the invention relate generally to bioassay systems and examples including methods, systems, and apparatuses employing sedimentation forces for conducting a sandwich assay.

BACKGROUND

Quantification of biomolecules including proteins, nucleic acids, and others from patient samples is an important area of research and commercial development. Assays for biomolecules (also referred to as bioassays herein) may be conducted to diagnose diseases, manage chronic conditions, and monitor the overall health of patients.

Sandwich assays are an example technique for conducting bioassays, which generally proceed by adsorbing a target analyte onto a surface coated with a capture agent. The target analyte is then detected using a detection agent that also binds to the target analyte at a different site than the capture agent. Signal from the detection agent is used to detect the target analyte.

BRIEF DESCRIPTION OF THE DRAWINGS

FIG. 6 shows an illustration depicting improvements in signal emission which may be achieved using the examples described herein.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Sandwich assays may be conducted using sedimentation techniques. In the case of sedimentation bioassays, rather than using a flat surface, the surfaces of beads may be used to conduct the sandwich assay. Co-pending application U.S. application Ser. No. 12/891,977, entitled "Devices, Systems, and Methods for Conducting Sandwich Assays Using Sedimentation", which is incorporated herein by reference in its entirety for any purpose, describes examples of sedimentation techniques and devices for conducting such sandwich assays.

Sandwich assays conducted according to the systems and methods described herein may offer orders of magnitude improvements in the sensitivity of bioassays, and may accordingly provide highly sensitive and portable diagnostic assays, which may be able to detect analytes at lower concentrations than previously possible. While advantages of sandwich assays in accordance with embodiments of the present invention are described herein, it is to be understood that the advantages are provided to aid in understanding technology described herein, however not all embodiments of the present invention may exhibit all, or any, of the described advantages.

While sandwich assays are discussed in examples described herein, techniques described herein may be utilized in a variety of different assays involving sedimentation. Agglutination assays or simple sedimentation of particles, e.g. cells, are examples. Generally, assays in accordance with embodiments of the present invention include transporting a sedimentation particle that is more dense than a density medium through the density medium.

Embodiments of the present invention include systems, apparatus, and methods for conducting assays using sedimentation. Assays, such as sandwich assays, utilizing sedimentation as described herein may be used to detect and/or quantify an analyte in a sample.

Figure 1:
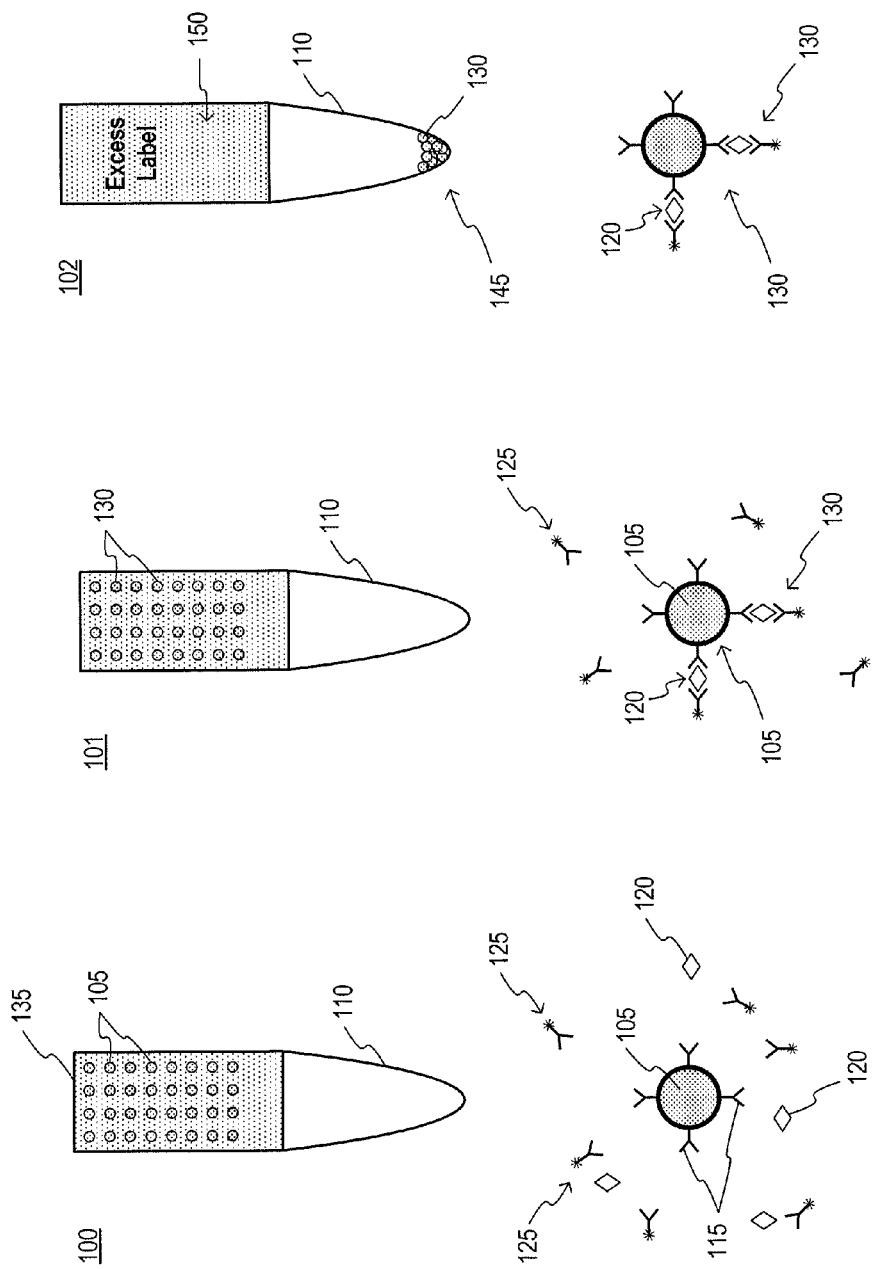
FIGS. 1A-1C are schematic illustrations of a sandwich assay including layering, incubation, and sedimentation.

FIGS. 1A-1C are schematic illustrations of a sequence of actions performed for a typical sedimentation assay. FIG. 1A illustrates layering 100, during which a sample 135 may be layered on a density medium 110. Prior to layering the sample on the density medium, sedimentation particles (e.g. beads)

105, detection particles 125, and capture agent 115 may be mixed with a biological fluid to form the sample 135. The target analyte (e.g. desired analyte) 120 may or may not be present in the sample 135. During incubation 101, as shown in FIG. 1B, the target analyte 120, if present, may bind to sites of the capture agent 115 on the surface of the sedimentation particles 105. Detection particles 125, which may include a labeling agent, may bind to the target analyte 120, forming complexes 130. FIG. 1C illustrates sedimentation 102 during which the sedimentation particles with target analyte and detection agent complexes 130 may be transported through the density medium 110 using sedimentation forces to form particle/bead pellet 145. The transportation of the sedimentation particles through the density medium may be facilitated by the sedimentation particles having a density greater than that of the density medium. As shown in FIG. 1C, excess detection agent 150 may remain in the sample. The free/unbound detection agent 150 which remains as excess in the sample is not representative of the presence of target analyte, because it is not bound to target analyte. Unbound detection agents may be less dense than the density medium, and may accordingly not be transported through the density medium responsive to sedimentation forces. The unbound detection agents may therefore remain at an interface between the density medium and the sample. As such, the unbound detection agent may generate noise and/or false positive signal for presence of the target analyte during the detection stage of the assay.

However, the above described technique may include certain shortcomings which may lead to insufficient sensitivity of the assay for label detection. One such limitation on the sensitivity of these assays may be a result of insufficient signal, background noise such as autofluorescence from device materials, and non-specific binding of labeling substances to the sedimentation particles giving false-positive signal. Systems and methods for conducting bioassays are described herein which may overcome some or all of these limitations and improve the sensitivity of the resulting assay.

Sandwich assays according to the present invention may be used to conduct immunoassays, gene expression assays, whole blood assays, or other desired bioassays. Any of a variety of suitable samples may be used including, but not limited to, whole blood, buffer solutions, or other biological fluid samples. The biological fluid may be combined with buffer or other fluids to form the sample. Generally, the sample may include analytes of interest (e.g. target analytes) to be detected and/or quantified in accordance with embodiments of the present invention.

Analytes of interest may include chemicals and/or molecules that are of interest for detection in a sample (e.g. target analytes). Any of a variety of analytes of interest may be detected in accordance with embodiments of the present invention, including proteins, RNA, and/or DNA.

Sandwich assays according to embodiments of the present invention may utilize sedimentation. Sedimentation generally refers to the process of movement of a particle or substance under an influence of a gravitational field. Sedimentation forces may be generated due to gravity or centrifugal forces, as examples.

Examples of sandwich assays described herein may be used to detect the presence of an analyte of interest (e.g. target analyte). Accordingly, a detection signal received from appropriate detection area may indicate the presence of the analyte of interest in the sample, as will be described further below. In some examples, the detection signal may be required to be above a threshold value to indicate presence of the analyte of interest in the sample to avoid possible false positives should some detection signal be received from the detection area due to other factors unrelated to the assay.

Examples of sandwich assays described herein may be used to quantify an amount of analyte of interest present in a sample. A magnitude or strength of a detection signal from an appropriate detection area may be indicative of the amount of analyte present in the sample.

Examples of sandwich assays utilizing sedimentation described herein may utilize sedimentation particles. Any particles suitable for conducting sandwich assays may be used, including, but not limited to, beads such as polystyrene beads or silica beads. Substantially any bead radii may be used. Examples of beads may include beads having a radius ranging from 150 nanometers to 10 microns. Other sizes may also be used.

The sedimentation particles (e.g. beads) may be coated with capture agents. The capture agents may be any suitable agents for binding to an analyte of interest. Suitable agents include antibodies for binding to one or more proteins, antigens, and mRNA probes for binding to DNA and/or RNA in a fluid sample. The capture agents may be coated on the particles in generally any suitable matter. In some examples, beads may be commercially available coated with appropriate capture agents.

Complexes formed in accordance with embodiments of the present invention may further include a detection agent (e.g. a tag) suitable for detection. Fluorescent tags (e.g. fluorophores) may provide an optical detection signal, however colorimetric or radioactive tags may also be used. Further improvements in labeling and enhanced sensitivity of signal during the detection stage may be obtained according to methods described herein and discussed in further detail below.

As mentioned, examples of sandwich assays utilizing sedimentation described herein may utilize density media. Density medium (also referred to as density media herein) is generally a liquid which may have a density selected based on the sample or sedimentation particles, as described further herein. The density media may generally be implemented using a fluid having the selected density. In some examples, a fluid sample may be diluted for use with a particular density media. The density media may include, for example, a salt solution containing a suspension of silica particles which may be coated with a biocompatible coating. An example of a suitable density media is Percoll™, available from GE Lifesciences. Particular densities may be achieved by adjusting a percentage of Percoll™ in a salt solution. More generally, viscosity and density may be adjusted by changing a composition of the media. Varying the concentration of solutes such as, but not limited to, sucrose or dextran, in the density media, may adjust the density and/or viscosity of the media. In some embodiments, the density media may include a detergent, such as Tween 20. The detergent may enhance a wash function of transport through the density media.

Figure 2:
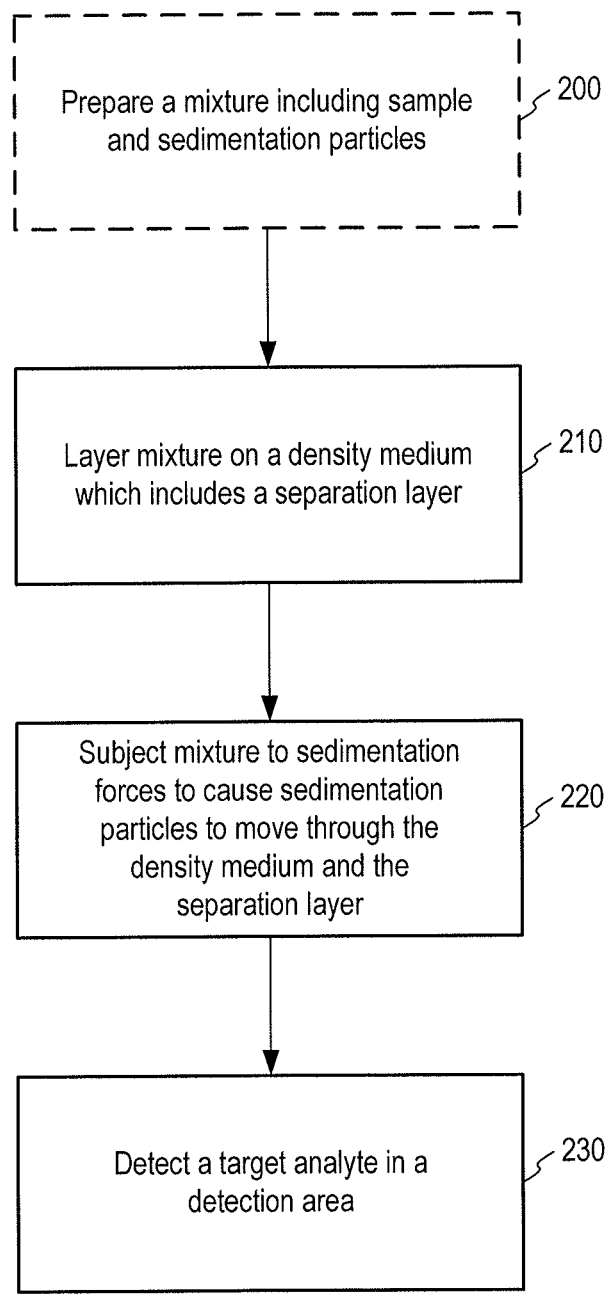
FIG. 2 is a flowchart of an example method for conducting sandwich assays according to embodiments of the present invention.

FIG. 2 is a flowchart of an example method for conducting sandwich assays according to embodiments of the present invention. Example methods according to embodiments of the present invention may include using a layer of hydrophobic liquid to separate and stabilize the interface between the sample and a density medium prior to the initiation of a sedimentation assay. The hydrophobic liquid may have a similar density to water, for example, silicon oil may be used. In some examples, a volume of hydrophobic liquid denser than water, e.g. a perfluorocarbon, may be used to stabilize a pellet of sedimentation particles in a detection area following the completion of a sedimentation assay.

Referring now to FIG. 2, an example method may include preparing a mixture including a sample and sedimentation particles, as shown in block 200. The sedimentation particles may be coated with capture agents to facilitate binding of analyte and labeling agent to the sedimentation particles. The sedimentation particles may be further coated or treated as described herein to enhance the sensitivity of the assay. Block 200 may be optional in some examples. In block 210, the mixture may be layered on a density medium, which is provided in an assay area, which may be a vial or a sedimentation channel. The assay areas may also include a separation layer, which may be configured to stabilize and/or increase the sensitivity of the assay, as will be further described below. In block 220, the mixture may be subjected to sedimentation forces, which may be due to natural gravity, or centrifugal forces. Other methods for inducing sedimentation forces may be used, such as electromagnetic forces for example. As shown in block 220, the sedimentation forces may cause the sedimentation particles to move through the density medium and the separation layer. The separation layer may be provided such that it is adjacent to the density medium. In some examples, the separation layer may be adjacent to a first region of the density medium and the mixture, which may reduce unwanted diffusion or mixture of mixture components into the density medium. In some examples, the separation layer may be provided adjacent to a second region of the density medium, which may be used to reduce unwanted diffusion or movement of sedimented particles away from a detection area. Upon completion of sedimentation, a target analyte, if present, may be detected in a detection area of the assay area (e.g. sedimentation channel), as shown in block 230. As will be appreciated, some of the steps may be omitted or additional steps may be added as appropriate for the specific application.

Figure 3A:
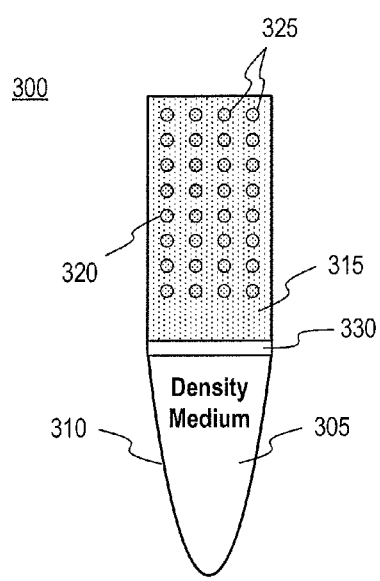
FIGS. 3A-3B are schematic illustrations of different stages of an example sandwich assay in accordance with embodiments of the present invention.
Figure 3B:
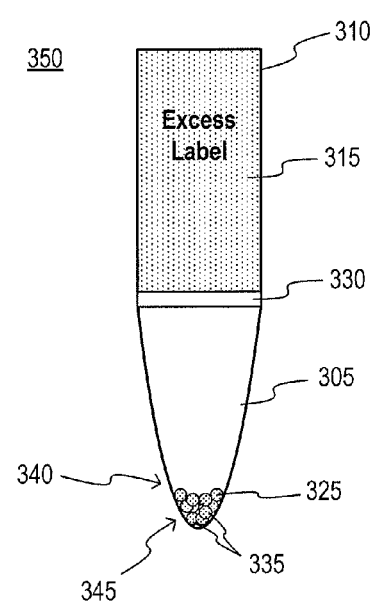

FIGS. 3A-3B are schematic illustrations of different stages of an example assay in accordance with embodiments of the present invention. FIG. 3A shows an example pre-sedimentation sandwich assay 300 according to examples of the present disclosure, which assay may include a density medium 305 disposed in a vial or a sedimentation channel 310. A sample 315 may be layered over the density medium 305. The sample 315 may include sedimentation particles 320 which may be treated or coated with a capture agent. The sample may further include target analyte, and detection particles (e.g., a labeling agent). As described previously with reference to FIGS. 1A-1C, if analyte of interest is present, complexes or aggregates 325 may form such that analyte and consequently detection particles bind to specific sites on surfaces of the sedimentation particles 320 (e.g., analyte binds to sites where capture agent is present, and detection particles bind to sites where analyte is present). The complexes 325 including the sedimentation particles may then be subjected to sedimentation forces, which may be forces due to gravity or forces generated by a centrifuge, as examples.

In example assays, multiple sedimentation particles may be present, including one population of sedimentation particles having a density greater than a density of the density medium and another population of sedimentation particles having a density less than a density of the density medium. The sedimentation particles may be coated with capture agents having an affinity for multiple sites of the target analyte, facilitating formation of complexes with target analytes bound to both sedimentation particle types. The sedimentation particles less dense than the density medium may include the labeling agent. Accordingly, the labeling agent may be transported to a detection area through the density medium responsive to sedimentation forces only when the detection label is bound in an aggregate with the target analyte.

In example particle counting assays, particles more dense than the density medium may be sedimented through the density medium into a pellet, and the volume of the pellet may correlate with the amount of particles present in the sample.

Referring again to FIGS. 3A-3B, assays may also include a separation layer 330. The separation layer may be a hydrophobic layer. In some examples, the separation layer 330 may include a hydrophobic material, such as organic or mineral oil, and the separation layer may be provided in the form of a fluid/liquid layer. In other examples, the separation layer 330 may be a media which is not hydrophobic, but is stabilized for an extended time period by virtue of high viscosity. In other examples the separation layer 330 may contain charged or water ordering polymers or salts in a non-hydrophobic water based medium. Examples of water ordering polymers include but are not limited to polyethylene glycol and dextran which may cause stable separation of non-hydrophobic media. The separation layer 330 may include a material which is denser than the sample 315 but less dense than the density medium 305. In this manner the separation layer 330 may naturally settle between the sample 315 and density medium 305. Because a hydrophobic material may be used, in some examples, the hydrophobic properties of the separation layer 330 may enhance the natural tendency of the separation layer to stabilize and not to mix with the adjacent two layers, which may be provided as aqueous solutions. The separation layer 330 may in this manner operate to "float" the biological sample 315 over the density medium 305, thus reducing intermixing and resulting distortions in the detection stages of the assay. Once sedimentation forces are applied, particles in the sample denser than the density medium may be driven through the separation layer and density medium.

As can be appreciated, biological fluids generally include water, containing a relatively small weight fraction of dissolved salts and biomolecules. Therefore biological fluids may tend not to form stable mixtures with hydrophobic fluids such as vegetable or mineral oils. Therefore, using a separation layer which includes a hydrophobic fluid may provide an effective boundary between two water based fluids even over prolonged periods of time. Furthermore, because the sedimentation particles 320 are selected to be denser than the density medium and separation layer material, the sedimentation particles may travel through the separation layer and travel through the density medium to the detection region 340.

FIG. 3B shows a schematic illustration of a post-sedimentation stage 350 of the assay 300 of FIG. 3A described above. Upon completion of sedimentation, the particles and complexes 325 may form a particle pellet 335 at the bottom or an end portion 345 of the sedimentation channel 310, which may be the detection area. In some examples, excess detection particles may remain in the sample 315 depending on the quantity of analyte present, for example. However, in contrast to assays which do not include separation layer, the separation layer 330 in the present example may effectively stabilize the sample adjacent to the density medium such that the excess label in the sample may not interfere significantly or generate noise during the detection stage of the assay.

Figure 4A:
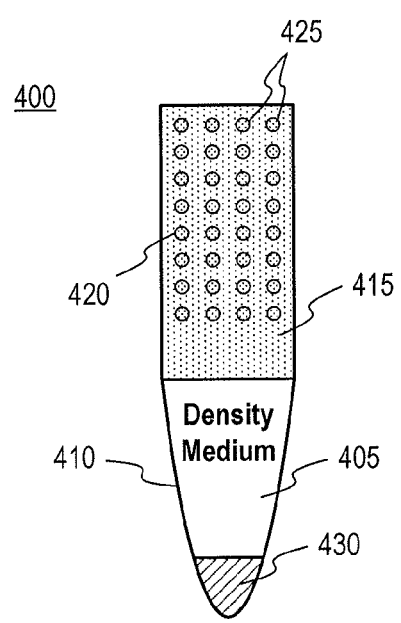
FIGS. 4A-4B are schematic illustrations of different stages of another example sandwich assay in accordance with embodiments of the present invention.
Figure 4B:
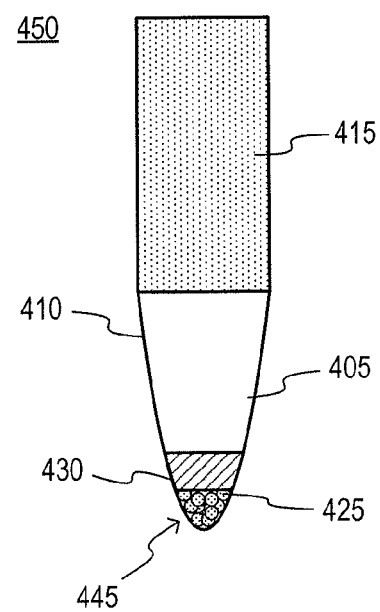

FIGS. 4A-4B are schematic illustrations of different stages of another example sandwich assay in accordance with embodiments of the present invention. The sandwich assays 400 and 450 may include a density medium 405 and a sample 415, which sample may include sedimentation particles 420, analyte, capture agent and labeling agent. As previously described, complexes 425 may form on surfaces of the particles 420 based in part on affinity between the capture agent, analyte, and labeling agent.

Similar to the examples shown in FIGS. 3A-3B, the assay 400 may include a separation layer 430. In some examples, the separation layer 430 may include a material which is denser than the density medium but less dense than the sedimentation particles. In some example, the separation layer may include a hydrophobic material, such as a vegetable or mineral oils. In some examples, the separation layer may include fluoroalkanes, such as perfluorodecalin, or it may include silicon oils, such as PDMS. In other examples, the separation layer 430 may be a media which is not hydrophobic, but is stabilized by virtue of high viscosity. In other examples the separation layer 430 may contain charged or water ordering polymers or salts in a non-hydrophobic water based medium. Examples of water ordering polymers include but are not limited to polyethylene glycol and dextran which may cause stable separation of non-hydrophobic media. In examples where the separation layer is selected to be denser than the density medium, the separation layer may settle to the bottom or end portion 445 of the assay area 410 (e.g. sedimentation channel), as shown in FIG. 4A. The sedimentation layer denser than the density medium may protect the sedimentation particles once sedimented into a pellet, from diffusing or otherwise moving away from the pellet, including once the sedimentation forces (e.g. centrifugal forces) had been removed.

In some examples, the sandwich assay may include both a first separation layer and a second separation layer, the first separation layer acting as a boundary between the sample and density medium and the second separation layer providing a boundary over the sedimentation particles. As will be understood, any and all examples of methods and apparatus for conducting sandwich assays may be used alone or in combination with each other as desired. As can be appreciated, using a separation layer as described herein can advantageously be used to stabilize bioassays during analysis and/or storage. In this manner, by stabilizing the sample and/or the particle pellet following the sedimentation stage may result in decreased background noise from diffusing label and provide for improved sensitivity of detection.

In some examples, the sedimentation particles may include particles which are denser than blood cells thereby providing enhanced separation from the sample. In some examples, the sedimentation particles may be silica microparticles.

Accordingly, examples have been described of the use of separation layers to improve assays employing sedimentation forces. Other techniques may additionally or instead be used in embodiments of the present invention with assays employing sedimentation forces. In some examples, particle charge may be used to enhance assays utilizing sedimentation forces. Examples of assays utilizing particle charge may also include use of the separation layer, described above, or may proceed without use of a separation layer. Examples of the use of particle charge are described further below.

Figure 5:
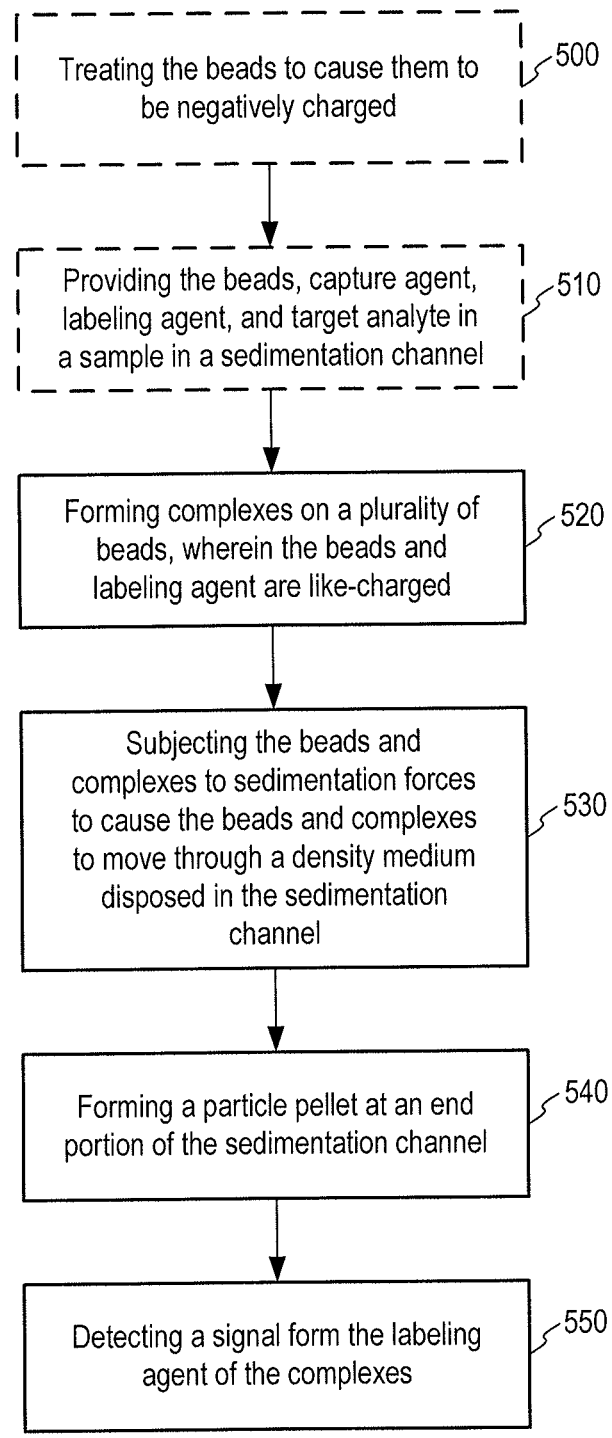
FIG. 5 is a flowchart of another example method for conducting sandwich assays according to embodiments of the present invention.

FIG. 5 is a flowchart of an example method for conducting sandwich assays according to embodiments of the present invention. In a first example method, a sandwich assay may be conducted using generally like-charged particles. In conventional sandwich assays, oppositely charged sedimentation particles and detection particles may be used. These oppositely charged particles attract each other which may result in non-specific binding (e.g. binding between the sedimentation particle and detection particle in the absence of an analyte). Non-specific binding may result in false-positive signal and may therefore reduce the sensitivity of the assay. In contrast, in some examples of the present disclosure, like-charged sedimentation particles and detection particles may be used. As can be understood, the like-charged particles may repel each other absent the presence of analyte which binds at the capture sites. The like-charged particles may therefore only bind in the presence of an analyte-mediated interaction and increase assay sensitivity.

Referring to FIG. 5, an example method of conducting an assay according to embodiments of the present disclosure includes forming complexes on a plurality of sedimentation particles in a fluid sample within an assay area (e.g. sedimentation channel), wherein individual ones of the complexes include a capture agent, a target analyte, and a labeling agent, and wherein the particles and the labeling agent have like charges, as shown in block 520. The sedimentation particles including complexes of capture agent, target analyte and labeling agent may then be subjected to sedimentation forces to cause the particles and complexes formed thereon to move to be transported through the density media, as in block 530. In some examples, the transporting or causing the particles to be transported through the density medium may include spinning a substrate which at least partially support the fluid sample containing the sedimentation particles. In some examples, transporting the particles and complexes through the density medium may occur at least in part due to gravitational forces. The method may further include forming a particle pellet at an end portion of the sedimentation channel and detecting a signal from the labeling agent of the complexes, as in blocks 540 and 550.

In some examples, the sedimentation particles may include particles that have a negatively charged surface. In some examples, the method may further include, prior to providing the sedimentation particles in the fluid sample, treating the sedimentation particles with carboxylate such that the sedimentation particles become negatively charged, as shown in box 500. These negatively charged sedimentation particles may be used in assays for negatively-charged target analyte and in conjunction with negatively charged labeling agents. In some examples, the method may include forming the sedimentation particles from negatively charged compounds, such that the resulting sedimentation particles are negatively charged and/or have a negative surface charge. In some examples, the particles may include polystyrene beads or silica beads. In some examples, the particles may have a diameter of about 0.15 microns. In some examples, the particles may have a diameter of up to about 10 microns. In some examples, the labeling agent may include carboxylate-modified fluorescent particles. In other examples, the labeling agent may be negatively charged dye molecules.

As can be appreciated in light of the above example, the methods disclosed may decrease non-specific binding of labeling substances to the assay particles. As various particles suspended in a fluid may tend to attract or repel one another due to their surface charges, using a labeling substance and sedimentation particles with opposite surface charges may cause them to attract despite the absence of analyte (e.g., resulting in non-specific binding of the label to the particles). Accordingly, the methods and systems described may reduce non-specific binding by using a labeling agent and sedimentation particles which have a same charge. In some examples, sedimentation particles or beads may be used which have negative charge or which are pretreated to have a negative surface charge. This may be particularly advantageous because human cells have a negative surface charge and using negatively charged beads may reduce the non-specific binding of the particles and labels to cells contained in the sample of interest rather than the biomolecules being analyzed.

In some examples of the present invention, labeling agents may be used that may improve the assay sensitivity. For example, the labeling agent may include detection particles or tags which have fluorescence emission that differs in wavelength from light used to excite the particle pellet during detection. In some examples, the detection particles (e.g. tags) may be nanoparticle fluorophores. In some examples, the detection particles may be quantum dots. In some examples, the detection particles may be polymer nanoparticles doped with energy transferring fluorescent dyes. Example assays using certain fluorescent tags, such as quantum dots, may advantageously increase the sensitivity of the assay by both decreasing non-specific binding (as described above due to the negative surface charge of the quantum dots) and by providing higher intensity emission. In some examples, signal emission of the labeling agent may be up to 100 times greater than emission obtainable from conventional dye molecules. Furthermore, and as depicted in FIG. 6, background noise may be reduced as described herein. In some examples, the labeling agent may include particles selected to have a large spectral gap between their excitation and fluorescent emission wavelengths. As will be appreciated, material autofluorescence may have a small spectral gap allowing for the autofluorescence to be filtered out, for example by using a large spectral gap detector.

As previously described, assays according to these examples, may be conducted by layering a mixture on a density medium disposed in an assay area (e.g. sedimentation channel or vial). Prior to layering, the mixture may be prepared by combining fluorescent tags. In some examples, the fluorescent tags may be nanoparticles selected to have higher individual fluorescent emission than dye molecules and have sufficiently large spectral gaps to allow for filtering material autofluorescence.

Figure 7:
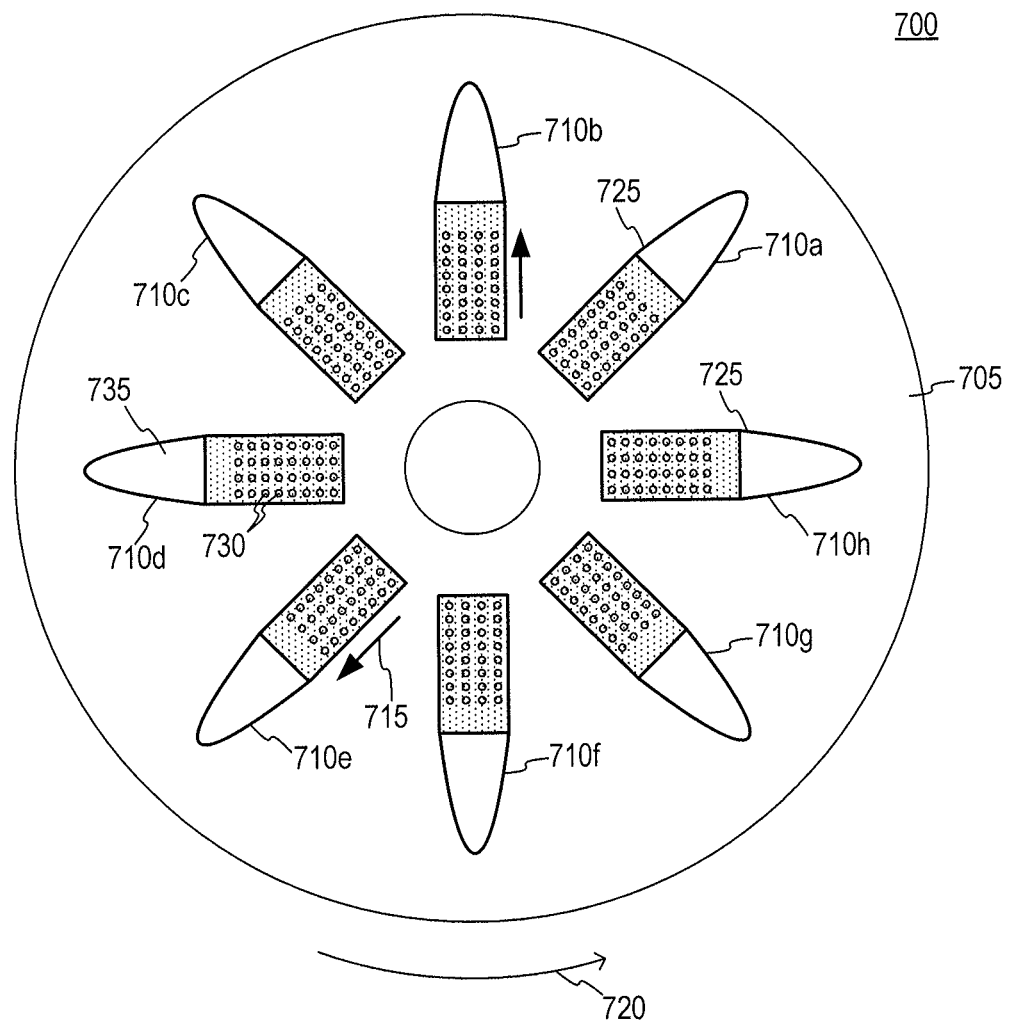
FIG. 7 is a schematic illustration of a microfluidic device arranged in accordance with an embodiment of the present invention.

FIG. 7 is a schematic illustration of a device arranged in accordance with an embodiment of the present invention. As described herein, a density medium 735 may be selected to have lower density than sedimentation particles 730 such that when subjected to sedimentation forces, the sedimentation particles travel to a detection area (e.g. sink to the bottom or travel to an end portion of a sedimentation channel). In some examples, sedimentation forces may be applied by way of gravitational forces. In some examples, centrifugal forces may be used as described, for example, with reference to FIG. 7.

A disk 700 may include a substrate 705 which may at least partially define regions of assay areas 710a-710h. While disks are described as example devices herein, it is to be understood that other embodiments of the present invention may employ different devices (e.g. vials) for conducting assays. The disk 700 may also include one or more fluid inlet ports (not shown) in fluid communication with the assay areas 710a-710h. During operation, as will be described further below, fluids including sample liquids, density media, and/or sedimentation particles, which may be suspended in a fluid, may be transported using centrifugal force from a generally central region of the disk 700 toward a periphery of the disk 700 in a direction indicated by an arrow 715. The centrifugal force may be generated by rotating the disk 700 in a direction indicated by the arrow 720, or in the opposite direction.

The substrate 705 may be implemented using any of a variety of suitable substrate materials. In some embodiments, the substrate may be a solid transparent material. Transparent plastics, quartz, glass, fused-silica, PDMS, and other transparent substrates may be desired in some embodiments to allow optical observation of sample within the channels and chambers of the disk 700. In some embodiments, however, opaque plastic, metal or semiconductor substrates may be used. In some embodiments, multiple materials may be used to implement the substrate 705. The substrate 705 may include surface treatments or other coatings, which may in some embodiments enhance compatibility with fluids placed on the substrate 705. In some embodiments surface treatments or other coatings may be provided to control fluid interaction with the substrate 705. While shown as a round disk in FIG. 7, the substrate 705 may take substantially any shape, including rectangular, hexagonal or other shapes, and the assay areas 710 may be arranged in any radial pattern as desired.

In some embodiments, as will be described further below, the substrate 705 may itself be coupled to a motor for rotation. In some embodiments, the substrate may be mounted on another substrate or base for rotation. For example, a microfluidic chip fabricated at least partially in a substrate may be mounted on another substrate for spinning. In some examples, the microfluidic chip may be disposable while the substrate or base it is mounted on may be reusable. In some examples, the entire disc may be disposable. In some examples, a disposable cartridge including one or more microfluidic channels may be inserted into disk or other mechanical rotor that forms part of a detection system.

The substrate 705 may generally, at least partially, define a variety of fluidic features. The fluidic features may be microfluidic features. Generally, microfluidic, as used herein, refers to a system, device, or feature having a dimension of around 1 mm or less and suitable for at least partially containing a fluid. In some embodiments, 500 µm or less. In some embodiments, the microfluidic features may have a dimension of around 100 µm or less. Other dimensions may be used. The substrate 705 may define one or more fluidic features, including any number of channels, chambers, inlet/outlet ports, or other features.

Disk 700, which may be a microfluidic disk, may be fabricated using microscale fabrication techniques, generally known in the art. For example, microscale fabrication techniques employed for manufacturing disk 700 may include embossing, etching, injection molding, surface treatments, photolithography, bonding and other techniques.

One or more fluid inlet ports (not shown) may be provided to receive a fluid that may be analyzed using the disk 700. The fluid inlet port may have generally any configuration, and a fluid sample may enter the fluid inlet port utilizing substantially any fluid transport mechanism, including pipetting, pumping, capillary action, or others. The fluid inlet port may take substantially any shape. Generally, the fluid inlet port is in fluid communication with at least one assay area 710, and may be in fluid communication with multiple assay areas, or individual other fluid inlet ports may be independently in fluid communication with respective assay areas 710a-710h. Generally, by fluid communication it is meant that a fluid may flow from one area to the other, either freely or using one or more transport forces and/or valves, and with or without flowing through intervening structures.

The assay areas 710a-710h may be implemented according to any and combinations of the examples described herein and/or may also incorporate other features for conducting sandwich assays known in the art. The assay areas 710a-710h may generally include one or more sedimentation channels 725 in fluid communication with the fluid inlet port (not shown). Although eight assay areas 710a-710h are shown in FIG. 7, generally any number may be present on the disk 700, which may be a microfluidic disk.

As the disk 700 is rotated in the direction indicated by the arrow 720 (or in the opposite direction), a centrifugal force may be generated. The centrifugal force may in part aid in transporting fluid and/or particles 730 from one portion of a sedimentation channel 725 to another portion of the sedimentation channel 725.

Figure 8:
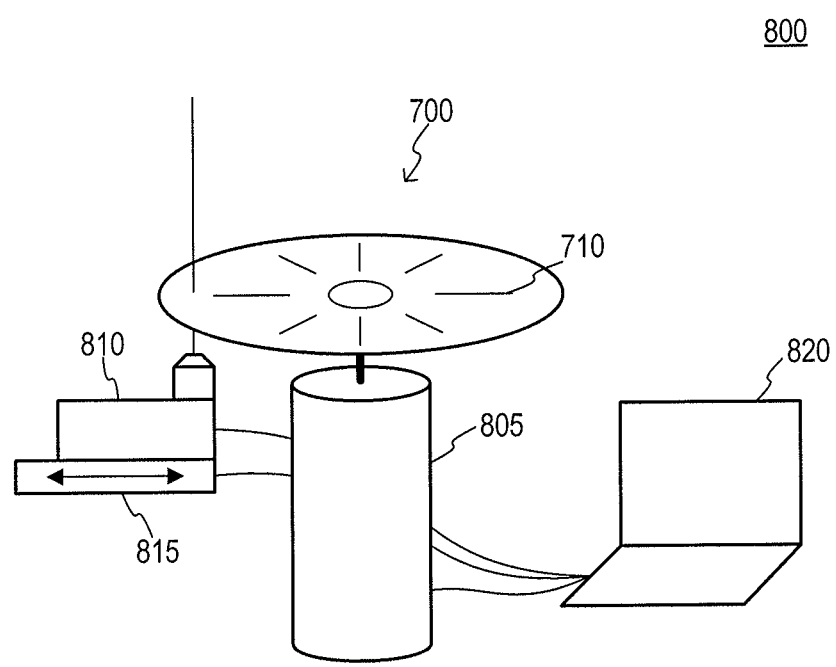
FIG. 8 is a schematic illustration of a system according to an embodiment of the present invention.

FIG. 8 is a schematic illustration of a system according to an embodiment of the present invention. The system 800 may include the device 700 of FIG. 7 with one or more assay areas 710. The assay areas 710 may be implemented according to any one or combinations of the example assays described herein. The device 700 may be coupled to a motor 805, which may be configured to spin the device 700, thereby generating centrifugal forces. A detection module 810 may be positioned to detect signal from labels in a detection region of the assay area 710, as will be described further below. An actuator 815 may be coupled to the detection module 810 and configured to move the detection module along the detection region in some examples. A processing device 820, e.g. a computer, controller, or the like, may be coupled to the motor 805, the detection module 810, and/or the actuator 815 and may provide control signals to those components. The processing device 820 may further receive electronic signals from the detection module 810 corresponding to the label signals received by the detection module 810. The processing device 820 may allow for automated control of the motor 805 and detection module 810 such that multiple assays on the device 700 may be automated and/or conducted in parallel on the device 700. All or selected of the components shown in FIG. 8 may be enclosed in an enclosure in some examples. In some examples, the device 700 may be a disposable microfluidic disk. Disposable microfluidic disks may be consecutively placed on and removed from the motor 805, such that multiple disks may be analyzed by the system 800.

The motor 805 may be implemented using a centrifugation and/or stepper motor. The motor 805 may be positioned relative to the detection module 810 such that, when the device 700 is situated on the motor 805, the disk is positioned such that a detection region of the assay area 710 is exposed to the detection module 810. That is, the motor may be configured such that it provides sufficient clearance for operation of the system 800 and access to detection regions of the assays.

The detection module 810 may include a detector suitable for detecting signal from labels on the coated particles described herein. The detector may include, for example, a laser and optics suitable for optical detection of fluorescence from fluorescent labels. The detection module may include one or more photomultiplier tubes. In other examples, other detectors, such as electronic detectors, CCD cameras, or other cameras (e.g. cell phone cameras), may be used. The actuator 815 may move the detector in some examples where signal may be detected from a variety of locations of the microfluidic device 700, as will be described further below.

The processing device 820 may include one or more processing units, such as one or more processors. In some examples, the processing device 820 may include a controller, logic circuitry, and/or software for performing functionalities described herein. The processing device 820 may be coupled to one or more memories, input devices, and/or output devices including, but not limited to, disk drives, keyboards, mice, and displays. The processing device may provide control signals to the motor 805 to rotate the device 700 at selected speeds for selected times, as has been described above. The processing device may provide control signals to the detection module 810, including one or more detectors and/or actuators, to detect signals from the labels and/or move the detector to particular locations. The processing device may develop these control signals in accordance with input from an operator and/or in accordance with software including instructions encoded in one or more memories, where the instructions, when executed by one or more processing units, may cause the processing device to output a predetermined sequence of control signals. The processing device 820 may receive electronic signals from the detection module 810 indicative of the detected signal from labels. The processing device 820 may detect an analyte of interest and/or calculate a quantity of a target analyte in a fluid sample based on the signals received from the detection module 810, as has been described above. Accordingly, the processing device 820 may perform calculations. The calculations may be performed in accordance with software including one or more executable instructions stored on a memory causing the processing device to perform the calculations. Results may be stored in memory, communicated over a network, and/or displayed. It is to be understood that the configuration of the processing device 820 and related components is quite flexible, and any of a variety of computing systems may be used including server systems, desktops, laptops, controllers, and the like.

As will be understood, while the examples presented herein have been described with reference to a single set of particle beads and respective analyte, multiple analytes may be included in a given assay and analyzed simultaneously, by using, for example, different bead sizes and densities of the beads and medium or layers of density medium. The methods for enhancing the sensitivity of sandwich assays may be applied in conducting any of assays described herein or known in the art.

Figure 9:
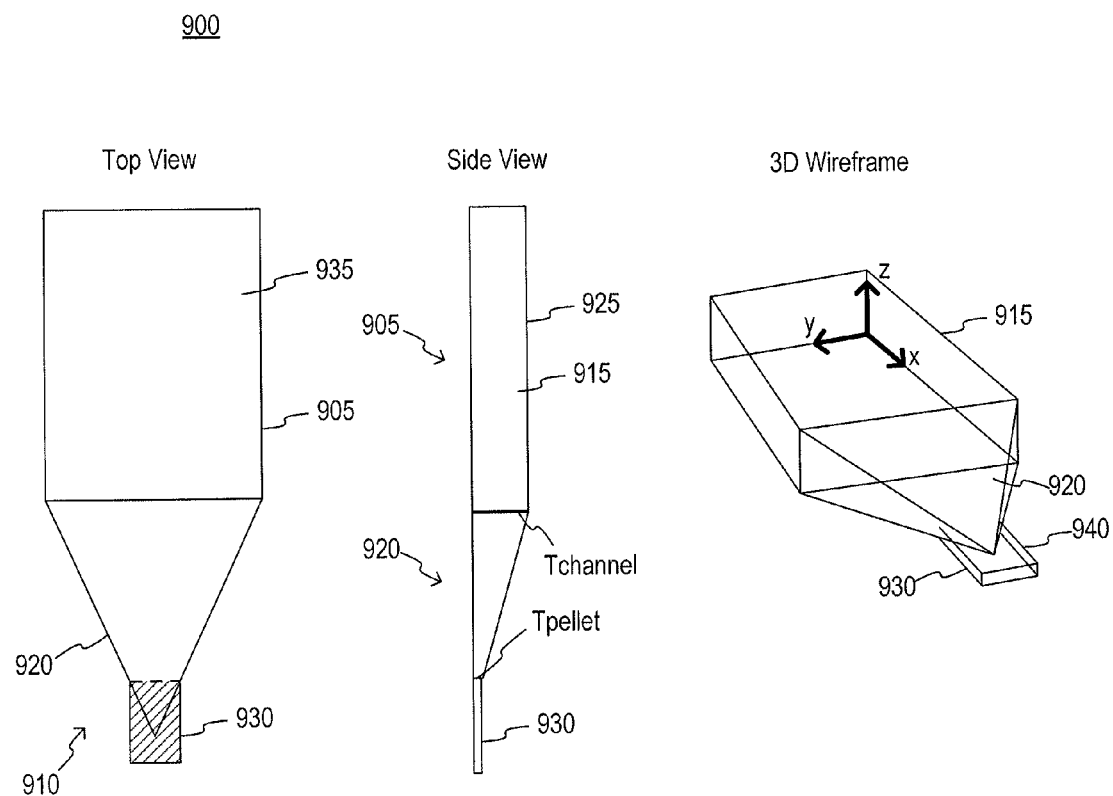
FIG. 9 shows another example microfluidic device according to embodiments of the present invention.

FIG. 9 includes a top view, side view, and three-dimensional wireframe view of another example device having a tapered detection region according to embodiments of the present invention. The device 900 may include an assay area (e.g. sedimentation channel 905 with a detection region 910). The channel 905 may include a pair of side walls 915, a bottom wall 925, and a top wall 935, and may have a generally rectangular cross-section. Other cross-sectional profiles, such as a triangular, trapezoidal, semi-circular, or other rounded profiles are possible and may be selected based on the specific fabrication technique used.

The sedimentation channel 905 may taper along a first direction Y so as to form generally triangularly shaped region at a bottom portion 920 of the device, the prism region having a first thickness $T_{channel}$. The sedimentation channel 905 may taper along a second direction Z so as to modify the generally prism-shaped bottom portion 920 into a generally pyramid shaped region 920. In some examples, the bottom portion 920 may include an end portion 940, which may have a substantially flattened rectangular profile. It will be understood that while a rectangular end portion 940 is shown, other form factors may be used such as a flattened semicircular end portion 940. Any shape which effectively reduces one dimension of (e.g. flattens) the particle pellet and thereby distributes the pellet over a larger surface area may be used.

In some examples, one or more of the walls 915, 925 and/or 935 of the sedimentation channel 905 may be sloped inward and/or upward to form the pellet chamber 930. The pellet chamber 930 may have a thickness $T_{pellet}$ which is less than the thickness $T_{channel}$. In some examples, the channel thickness $T_{channel}$ may be reduced as compared to the thickness $T_{pellet}$ by a factor of ½ to 1/10. That is, in some examples, the thickness $T_{channel}$ may be twice as thick as the thickness $T_{pellet}$. In some examples, the thickness $T_{channel}$ may be up to about 10 times the thickness $T_{pellet}$ of the pellet chamber 930. As can be appreciated, the narrowing of the thickness of the channel 905 causes the particle pellet to spread out and may lead to an increase in the effective signal of the sedimentation assay. In some examples, the thickness $T_{pellet}$ of the pellet chamber 930 may be constant throughout the length of the chamber 930. In some examples, the thickness of the pellet chamber may vary along its length.

As will be appreciated, packed particles may reflect light signals due to Rayleigh or Mie scattering depending on size. Thick particle pellets may be less efficient at transmitting light as compared to thinner pellet with a large surface area, which may be more effective at transmitting light-based signals such as fluorescence, luminescence, or phosphorescence. Examples according to the present disclosure, such as the example device 900, may provide a larger surface area for detection thereby increasing the sensitivity of the assay, as described. Furthermore, low cost instrumentation, for example such that use large area light collection optics, may be used to detect the larger effective signal from a thinner pellet provided according to the examples described As described, examples of devices according to the present invention may include detection regions 910 which may be tapered and/or flattened to provide a pellet chamber 930 with an increased surface area. As will be appreciated, a non-tapered or constant thickness configuration may generally provide a detection region causes the detection particles to gather and/or clump together to form a pellet having a smaller cross sectional area and larger thickness than the device 900. This may decrease the sensitivity of the assay because the smaller cross-sectional area will generally provide a weaker detection signal.

An example method for conducting a bioassay may include layering a mixture on a density medium disposed in a sedimentation channel, wherein the mixture includes a sample and coated particles, subjecting the mixture to sedimentation forces such that particles denser than the density medium travel through the density medium, and forming a substantially flat particle pellet in a detection region of the sedimentation channel.

The method of conducting a bioassay may include the steps of transporting the particles and aggregates to an end portion of the sedimentation channel, wherein the end portion has a first length shorter than a length of the sedimentation channel, a first width shorter than the width of the sedimentation channel and a first thickness shorter than the thickness of the sedimentation channel. The method may further include the steps of detecting a presence of an analyte of interest in the detection region.

In some examples, the step of forming a substantially flat particle pellet may include collecting the particles in an end region of the sedimentation channel, the end region being tapered along a first direction and a second direction. In some examples, forming a substantially flat particle pellet may include forming a particle pellet which has a thickness and a length having a high aspect ratio.

Figure 10:
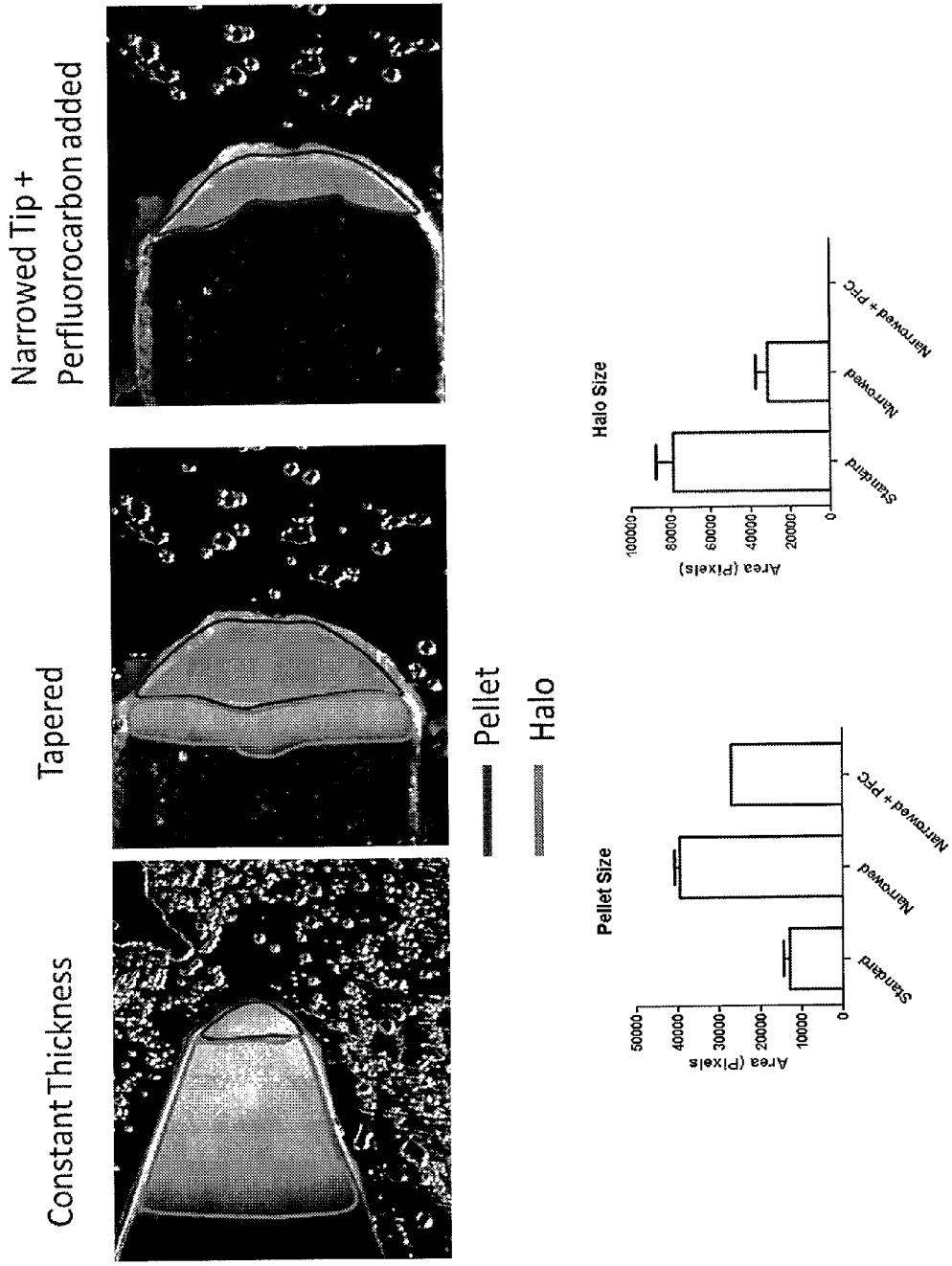
FIG. 10 shows examples of detection methods according to examples described herein.

Although improvements are described relative to typical assays, the advantages or improvements achieved by examples of the present invention are provided herein to aid in the understanding of the disclosure, and it is to be understood that not all embodiments of the present invention may provide all, or any, of the improvements or advantages described herein. FIG. 10 shows one example demonstrating improved sensitivity and detection of a bioassay conducted according to some of the examples described herein. The figures show an increased pellet area by using an example tapered channel geometry according to the present disclosure. The channel thickness is narrowed from 200 microns to 50 microns in the tapered region. The example in FIG. 10 further demonstrates stabilization of the pellet by using a hydrophobic fluid layer including perfluorocarbon to minimize the formation of a diffusion "halo".

From the foregoing it will be appreciated that, although specific embodiments of the invention have been described herein for purposes of illustration, various modifications may be made without deviating from the spirit and scope of the invention.

What is claimed is:

1. A microfluidic device for conducting an assay, the device comprising:
   a channel;
   a sample contained in the channel, wherein the sample includes sedimentation particles configured to cause an analyte of interest, if present, to bind to the sedimentation particles;
   a density medium contained in the channel, wherein the sedimentation particles have a density greater than a density of the density medium;
   a first separation layer fluid adjacent to the density medium, wherein the first separation layer fluid comprises a fluid liquid material which is denser than the sample but less dense than the density medium, the first liquid material positioned at an interface between the density medium and the sample; and
   a detection area arranged at an end portion of the channel, wherein the device is configured such that the sedimentation particles move to the detection area through the density medium and the first separation layer fluid responsive to sedimentation forces.

2. The device of claim 1, wherein the first separation layer fluid comprises a hydrophobic material.

3. The device of claim 1, wherein the first separation layer fluid comprises a mineral oil.

4. The device of claim 1, wherein the first separation layer fluid comprises an organic oil.

5. The device of claim 1, wherein the first separation layer fluid comprises a charged or water ordering polymer.

6. The device of claim 1, wherein the first separation layer fluid comprises a salt in a water based medium.

7. The device of claim 1, wherein the first separation layer fluid comprises a fluoroalkane fluid.

8. The device of claim 1, wherein the first separation layer fluid comprises a perfluorocarbon.

9. The device of claim 1, wherein the first separation layer fluid comprises a perfluoroalkane fluid.

10. The device of claim 1, wherein the sedimentation particles comprise at least one of polystyrene beads, polymethylmethacrylate beads, silica beads, or silica microparticles.

11. The device of claim 1, wherein the sample further comprises a labeling agent.

12. The device of claim 11, wherein the labeling agent includes quantum dots.

13. The device of claim 1, wherein the density medium is a liquid having a selected density.

14. A microfluidic device for conducting an assay, the device comprising:
   a channel;
   a sample contained in the channel, wherein the sample includes sedimentation particles configured to cause an analyte of interest, if present to bind to the sedimentation particles;
   a density medium contained in the channel;
   a first separation layer fluid adjacent to the density medium;
   a detection area arranged at an end portion of the channel, wherein the device is configured such that the sedimentation particles move to the detection area through the density medium and the first separation layer fluid responsive to sedimentation forces; and
   a second separation layer fluid in the channel.

15. The device of claim 14, wherein the first separation layer fluid comprises a first material which is denser than the sample but less dense than the density medium, wherein the second separation layer comprises a second material which is denser than the density medium but less dense than the coated particles, and wherein the first material is positioned between the density medium and the sample and the second material is positioned near the detection area.

16. The device of claim 1, wherein the sedimentation particles include a first plurality of sedimentation particles having a first density greater than a density of the density medium and a second plurality of sedimentation particles having a second density less than a density of the density medium such that at least some of the sedimentation particles remain in the channel on a side of the first separation layer fluid opposite the detection area when the sedimentation particles are subjected to sedimentation forces.

17. The device of claim 1, wherein the sedimentation particles include a first plurality of sedimentation particles having a first density greater than a density of the density medium and a second plurality of sedimentation particles having a second density less than a density of the density medium, wherein the second density is selected such that densities of individual complexes between the analyte of interest and sedimentation particles from the second plurality of sedimentation particles is greater than the density of the density medium, the second plurality of sedimentation particles including a labeling agent.

* * * * *